United States Patent
Bernstein et al.

(10) Patent No.: US 10,039,923 B2
(45) Date of Patent: Aug. 7, 2018

(54) NEURAL IMPLANT FOR MICROSTIMULATION

(71) Applicant: The Charles Stark Draper Laboratory, Inc., Cambridge, MA (US)

(72) Inventors: Jonathan Bernstein, Medfield, MA (US); Daniel Freeman, Reading, MA (US); Reed Irion, Belmont, MA (US); Brett Ingersoll, Everett, MA (US); Amy Duwel, Cambridge, MA (US); Andrew Czarnecki, Cambridge, MA (US); Brian Daniels, Boston, MA (US); Anilkumar Harapanahalli Achyuta, Cambridge, MA (US); Bryan McLaughlin, Cambridge, MA (US)

(73) Assignee: THE CHARLES STARK DRAPER LABORATORY, INC., Cambridge, MA (US)

( * ) Notice: Subject to any disclaimer, the term of this patent is extended or adjusted under 35 U.S.C. 154(b) by 82 days.

(21) Appl. No.: 15/014,675

(22) Filed: Feb. 3, 2016

(65) Prior Publication Data

US 2017/0216606 A1 Aug. 3, 2017

(51) Int. Cl.
*A61N 1/39* (2006.01)
*A61N 1/378* (2006.01)
(Continued)

(52) U.S. Cl.
CPC ......... *A61N 1/3785* (2013.01); *A61N 1/0551* (2013.01); *A61N 1/36125* (2013.01); *A61N 1/37205* (2013.01)

(58) Field of Classification Search
CPC ... A61B 1/041; A61B 1/00016; A61B 5/0071; A61N 1/0551; A61N 1/36125; A61N 1/37205; A61N 1/3785
See application file for complete search history.

(56) References Cited

U.S. PATENT DOCUMENTS

| | | | |
|---|---|---|---|
| 6,356,788 B2 | 3/2002 | Boveja | |
| 2006/0004423 A1* | 1/2006 | Boveja | A61N 1/08 607/46 |

(Continued)

FOREIGN PATENT DOCUMENTS

| | | |
|---|---|---|
| WO | 2007121265 A1 | 10/2007 |
| WO | 2014089299 A2 | 6/2014 |
| WO | 2015042558 A1 | 3/2015 |

OTHER PUBLICATIONS

International Search Report and Written Opinion dated Apr. 12, 2017 in PCT Application No. PCT/US2017/015603.

*Primary Examiner* — Michael D Abreu
(74) *Attorney, Agent, or Firm* — Lando & Anastasi, LLP

(57) ABSTRACT

This disclosure provides systems and methods for delivering a neural stimulation pulse. A neural implant device can include an energy harvesting circuit configured to receive an input signal and generate an electrical signal based on the received input signal. A diode rectifier in series with the energy harvesting circuit can rectify the electrical signal. The energy harvesting circuit and the diode rectifier can be encapsulated within a biocompatible electrically insulating material. A neural electrode can be exposed through the biocompatible electrically insulating material. The neural electrode can be configured to deliver a neural stimulation pulse. The neural implant device can have a volume that is less than about 1.0 cubic millimeter.

30 Claims, 5 Drawing Sheets

(51) Int. Cl.
*A61N 1/36* (2006.01)
*A61N 1/372* (2006.01)
*A61N 1/05* (2006.01)

(56) References Cited

U.S. PATENT DOCUMENTS

2007/0067004 A1 3/2007 Boveja et al.
2009/0157147 A1 6/2009 Cauller et al.

\* cited by examiner

NEURAL IMPLANT FOR MICROSTIMULATION

BACKGROUND

Electrical nodes can be implanted into the body of a patient for the purpose of stimulating nervous tissue. Typically, such devices include wired electrodes that receive energy from a source located outside the body. Implantable devices that connect to an external power source with wires are very invasive, and can cause long term damage to neural tissue. Wireless neural implants are available, but are often unable to provide neural stimulation pulses of sufficient voltage and current to effectively stimulate nervous tissue. Furthermore, when a plurality of wireless neural devices are implanted into a patient, it can be difficult to selectively control the individual devices.

SUMMARY

The systems, methods, and devices of the disclosure each have several innovative aspects, no single one of which is solely responsible for the desirable attributes disclosed herein.

One innovative aspect of the subject matter described in this disclosure can be implemented in a neural implant device. The neural implant device can include an energy harvesting circuit configured to receive an input signal and generate an electrical signal based on the received input signal. The neural implant device can include a diode rectifier in series with the energy harvesting circuit. The diode rectifier can be configured to rectify the electrical signal. The energy harvesting circuit and the diode rectifier can be encapsulated within a biocompatible electrically insulating material. The neural implant device can include a neural electrode exposed through the biocompatible electrically insulating material and configured to deliver a neural stimulation pulse. The neural implant device can have a volume that is less than about 1 cubic millimeter.

In some implementations, the neural implant device can have a volume that is less than about 0.5 cubic millimeters. In some implementations, the energy harvesting circuit can include an inductor in parallel with a capacitor. In some implementations, the inductor can have an inductance in the range of about 10 nH to about 500 µH.

In some implementations, the inductor can include a coil made from at least one of copper, aluminum, silver or gold wound around a ferrite core. The coil can be wound within the biocompatible electrically insulating material, and the biocompatible electrically insulating material can be substantially free from air bubbles. In some implementations, the biocompatible electrically insulating material can include at least one of parylene, silicone, and epoxy.

In some implementations, the inductor can have a diameter that is no greater than about 0.4 millimeters and a length that is no greater than about 1.0 millimeters. In some implementations, the capacitor can have a capacitance in the range of about 1 pF to about 10 nF. In some implementations, the capacitor and the inductor can form a circuit having a resonance frequency in the range of about 100 kHz to about 100 MHz. In some implementations, at least two of the capacitor, the inductor, and the diode rectifier are included on a single chip. In some implementations, the energy harvesting circuit can include at least one piezoelectric energy harvester.

In some implementations, the neural implant device can include an energy storage device configured to store a voltage from an output of the diode rectifier and a first switch configured to discharge the stored voltage to the neural electrode when the switch is in a closed position. In some implementations, the first switch can include at least one of a microelectromechanical systems (MEMS) magnetic reed switch or an electrostatically actuated MEMS switch. In some implementations, the first switch can be a normally open switch configured to close in response to a wireless actuation signal. In some implementations, the first switch can exhibit hysteresis, such that an amplitude of the wireless actuation signal required to close the switch is greater than an amplitude of the wireless actuation signal required to hold the switch in a closed position. In some implementations, the wireless actuation signal can include a DC component selected to be of sufficient to magnitude to hold the switch in a closed position and an AC component having a frequency that matches a resonant frequency of the switch. The sum of the amplitudes of the DC component and the AC component can be sufficient to close the switch.

In some implementations, the neural implant device can include an antenna coupled to the energy harvesting circuit. The antenna can be configured to receive the input signal from a transmitter and provide the input signal to the energy harvesting circuit.

Another innovative aspect of the subject matter described in this disclosure can be implemented in a method for stimulating muscle or nervous tissue. The method can include receiving, by an energy harvesting circuit, an input signal. The method can include converting, by the energy harvesting circuit, the input signal to an electrical signal. The method can include rectifying the electrical signal to provide a rectified signal to an energy store. The method can include discharging, by a switch, a stored voltage from the energy store to produce a neural stimulation pulse.

In some implementations, the method can include receiving, by the switch, a wireless actuation signal causing the switch to discharge the stored voltage from the energy store. In some implementations, the input signal can have a frequency in the range of about 100 kHz to about 100 MHz, and the actuation signal can have a frequency in the range of about 1 kHz to about 50 kHz. In some implementations, the energy harvesting circuit can include an inductor in parallel with a capacitor. In some implementations, the energy harvesting circuit can include at least one piezoelectric energy harvester.

Another innovative aspect of the subject matter described in this disclosure can be implemented in a system for stimulating muscle or nervous tissue. The system can include a power signal generator and a plurality of implantable devices. Each implantable device can include an energy harvesting circuit configured to receive an input signal from the power signal generator and generate an electrical signal based on the received input signal. Each implantable device can include a diode rectifier in series with the energy harvesting circuit and configured to rectify the electrical signal. The energy harvesting circuit and the diode rectifier can be encapsulated within a biocompatible electrically insulating material. Each implantable device can include an energy storage device configured to store a voltage from an output of the diode rectifier and a switch configured to discharge the stored voltage to a neural electrode when the switch is in a closed position. The system can include an actuation signal generator configured to generate actuation signals to selectively close the switches of the plurality of implantable devices.

In some implementations, the switch of a first one of the plurality of implantable devices can be configured to close in response to an actuation signal that differs from an actuation signal associated with the switch of at least a second one of the plurality of implantable devices. In some implementations, the system can include a controller configured to control the actuation signal generator and the power signal generator.

In some implementations, each of the implantable devices can have a volume that is less than about 0.3 cubic millimeters. In some implementations, the energy harvesting circuit of each of the plurality of implantable devices can include an inductor in parallel with a capacitor. In some implementations, at least two of the capacitor, the inductor, the diode rectifier, and the switch can be included on a single chip. In some implementations, the energy harvesting circuit of each of the plurality of implantable devices can include at least one piezoelectric energy harvester. In some implementations, the switch of each of the plurality of implantable devices can include at least one of a microelectromechanical systems (MEMS) reed switch or an electrostatically actuated MEMS switch.

BRIEF DESCRIPTION OF THE DRAWINGS

The skilled artisan will understand that the figures, described herein, are for illustration purposes only. It is to be understood that in some instances various aspects of the described implementations may be shown exaggerated or enlarged to facilitate an understanding of the described implementations. In the drawings, like reference characters generally refer to like features, functionally similar elements, and/or structurally similar elements throughout the various drawings. The drawings are not necessarily to scale. Instead, emphasis is placed upon illustrating the principles of the teachings. The drawings are not intended to limit the scope of the present teachings in any way. The system and method may be better understood from the following illustrative description with reference to the following drawings in which.

Like reference numbers and designations in the various drawings indicate like elements.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

This disclosure is generally related to systems and methods for delivering a neural stimulation pulse. More particularly, the systems and methods disclosed provide techniques for wirelessly stimulating neural tissue in a patient via one or more wireless neural devices implanted into the patient. In some implementations, each device can be configured to store a voltage, and the voltage can be discharged through nervous tissue adjacent to the device when a switch located on the device is closed. In some implementations, each device can be addressed individually from the other devices, such that subsets of the devices can be activated simultaneously.

Figure 1:
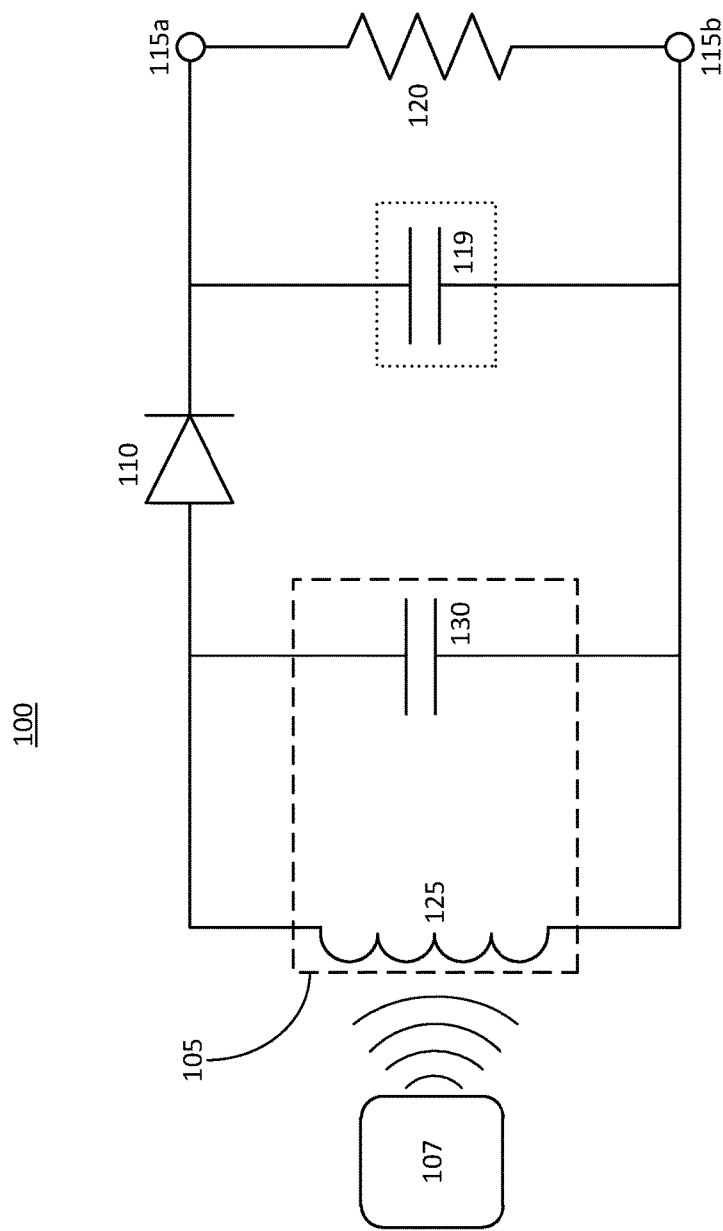
FIG. 1 shows a schematic diagram of an example neural implant device, according to an illustrative implementation.

FIG. 1 shows a schematic diagram of an example neural implant device 100, according to an illustrative implementation. The device 100 includes an energy harvesting circuit 105 in series with a diode rectifier 110. Electrodes 115a and 115b are positioned on either side of nervous tissue 120, which is modeled as a resistor. The electrodes 115a and 115b receive an electrical signal from the energy harvesting circuit 105 and diode rectifier 110, and deliver a neural stimulation pulse to the nervous tissue 120, which may include a muscle, a nerve or a bundle of nerves targeted for stimulation. The device 100 also may include a capacitor 119. The broken line surrounding the capacitor 237 indicates that the capacitor 237 is an optional component. A power signal generator 107 is configured to deliver an input signal to the energy harvesting circuit 105. The power signal generator 107 may be external to the body of the patient.

In the device 100 shown in FIG. 1, the energy harvesting circuit 105 is implemented as an inductor 125 in parallel with a capacitor 130. Together, the inductor 125 and the capacitor 130 can be configured to receive the signal from the power signal generator 107, and convert the received signal into an electrical signal. For example, in some implementations the power signal generator 107 can be configured to generate an input signal in the form of an applied magnetic field. The magnetic field generated by the power signal generator 107 can be selected to ensure that it can be efficiently transmitted through the body tissue of the patient to the energy harvesting circuit 105. In some implementations, the magnetic field generated by the power signal generator can have a frequency in the range of about 100 kHz to about 100 MHz. The magnetic field induces a variable voltage across the inductor 125, which resonates with the capacitor 130. Thus, the inductor 125 and the capacitor 130, which together form the energy harvesting circuit 105, generate an electrical signal in response to the signal received from the power signal generator 107.

In some implementations, the electrical characteristics of the inductor 125 and the capacitor 130 can be selected to provide electrical resonance at a frequency matching the frequency of the magnetic field generated by the power signal generator 107. In some implementations, the capacitor 130 may be a commercially available capacitor. The capacitor 130 can have a capacitance in the range of about 1 pF to about 10 nF. The inductor 125 can have an inductance in the range of about 10 nH to about 500 µH. In some implementations, the inductor 125 can be made from a coil of conductive material, such as copper, silver, aluminum, gold, or platinum. The coil can be wound around a ferrite core within a biocompatible hermetic insulating material, such as silicone, parylene, or epoxy. For example, an insulating material in liquid form, such as liquid silicone, can be dripped onto the inductor as the conductive coil is wrapped around the ferrite core. After the coil has been wound, the liquid insulating material can be cured. This process can help to reduce the likelihood of developing air bubbles within the insulating material. In some implementations, the ferrite core may have a diameter in the range of about 0.1 millimeters to about 0.3 millimeters. In some implementations, the inductor can have a diameter of less than about 0.6 millimeters, less than about 0.5 millimeters, less than about 0.4 millimeters, less than about 0.3 millimeters, or less than about 0.2 millimeters. The inductor can have a length of less than about 1.2 millimeters, less than about 1.1 millimeters, less than about 1 millimeter, less than about 0.9 millimeters, or less than about 0.8 millimeters.

Because the device 100 is implanted into a patient, smaller sizes for individual components may be preferable in order to minimize health risks and discomfort to the patient. For example, in some implementations, the entire implantable device 100 can have a volume of less than about 1 cubic millimeter, less than about 0.5 cubic millimeters, less than about 0.4 cubic millimeters, 0.3 cubic millimeters, or less than about 0.2 cubic millimeters. In some implementations, the implantable device 100 can have a volume of in the range of about 0.1 cubic millimeters to about 0.5 cubic millimeters. In some implementations, the device 100 can be generally cylindrical in shape, and may have a diameter in the range of about 0.3 millimeters to about 0.7 millimeters and a length in the range of about 1.3 millimeters to about 1.7 millimeters. In some implementations, the device may have a diameter of less than about 0.5 millimeters and a length of less than about 1.5 millimeters. In some other implementations, the device 100 may have another shape, such as a cube or a rectangular prism. In still other implementations, the device 100 may have an irregular shape.

It should be noted that, while FIG. 1 depicts the energy harvesting circuit 105 as an inductor 125 in parallel with a capacitor 130, the energy harvesting circuit 105 may also be implemented in other ways. For example, the energy harvesting circuit 105 can include a piezoelectric energy harvester. In general, a piezoelectricity is electrical charge that accumulates in a material in response to mechanical stress. Thus, a piezoelectric energy harvester can be configured to respond to a signal generated by the power signal generator 107 in a way that induces mechanical stress in the piezoelectric energy harvester, which in turn causes the piezoelectric energy harvester to generate an electrical charge. In some implementations, the energy harvesting circuit 105 can be implemented as a block of PZT, a piezoelectric microshell transducer, a piezoelectric bimorph, a piezoelectric monomorph, or any other type of piezoelectric energy harvesting device capable of generating an electrical signal in response to an input signal received from the power signal generator 107. In such implementations, the power signal generator 107 can be configured to produce a signal that induces mechanical stress in the piezoelectric energy harvester. For example, the piezoelectric energy harvester can be or can include an ultrasonic transducer, and the power signal generator 107 can generate an acoustic signal to be received by the piezoelectric energy harvester. The acoustic signal can induce stress in the piezoelectric energy harvester, which can then be converted into an electrical signal. Other types of energy harvesting devices also may be used as the energy harvesting circuit 105. For example, the energy harvesting circuit 105 can be or can include a photovoltaic energy harvester, a pyroelectric energy harvester, a thermoelectric energy harvester, or an electrostatic energy harvester.

Furthermore, the signal generated by the power signal generator 107 can be selected based in part on the characteristics of the components used to form the energy harvesting circuit 105. In some implementations, the signal generated by the power signal generator may include a near-field signal. In some other implementations, the signal generated by the power signal generator may include a far-field signal. In some implementations, the device 100 may include an antenna coupled to the energy harvesting circuit. The antenna can be configured to receive the signal from the power signal generator 107 and deliver the signal to the energy harvesting circuit 105.

As discussed above, the energy harvesting circuit 105 can be configured to convert a time-varying input signal from the power signal generator 107 into a time-varying electrical signal. In some implementations, the frequencies that are most efficient for transmitting the input signal to the device 100 through the body of a patient may be significantly higher than the frequencies of neural stimulation pulses that most efficiently excite the nervous tissue 120. As a result, the frequency of the electrical signal generated by the energy harvesting circuit 105 may be too high to efficiently stimulate nervous tissue 120, because the frequency of the electrical signal produced by the energy harvesting circuit 105 will be approximately equal to the frequency of the signal received from the power signal generator 107. To address this problem, the diode rectifier 110 is positioned in series with the energy harvesting circuit 105. The diode rectifier 110 receives the electrical signal from the energy harvesting circuit 105 and produces a rectified signal having a lower frequency (i.e., a low frequency moving average voltage proportional to the amplitude of the RF electrical signal received from the energy harvesting circuit 105). This lower frequency rectified signal is then delivered to the nervous tissue 120 via the electrodes 115a and 115b.

In some implementations, the electrical signal produced by the energy harvesting circuit 105 can have a relatively small magnitude. Therefore, the diode rectifier 110 may be selected to have a relatively low turn-on voltage and a low parasitic capacitance in order to efficiently convert the electrical signal from the energy harvesting circuit 105 to a rectified signal. For example, in some implementations the diode rectifier 110 may have a turn-on voltage of less than about 0.3 volts, less than about 0.2 volts, less than 0.1 volts, or less than about 0.05 volts. Example devices that may be suitable for use as the diode rectifier 110 can include an RF Schottky diode or an RF detector diode. In some implementations, including the optional capacitor 119 in the device 100 can help to turn on the diode at lower voltages. In some implementations, the capacitor 119 may have a capacitance in the range of about 100 pF to about 10 nF.

In some implementations, the electrodes 115a and 115b may be exposed to the nervous tissue 120 through an encapsulating layer that surrounds the other components of the implantable device 100. For example, the energy harvesting circuit 105 and the diode rectifier 110 can be encapsulated in a biocompatible material, such as parylene, silicone, epoxy, or any other non-toxic insulating material. The electrodes 115a and 115b can be electrically connected to the energy harvesting circuit 105 and the diode rectifier 110 as shown in the schematic of FIG. 1, but may be exposed through biocompatible encapsulation material to facilitate delivery of the neural stimulation pulse to the nervous tissue 120. The electrodes 115a and 115b can be formed from any non-toxic conductive material. In some implementations, the electrodes 115a and 115b may be formed from porous platinum. In some other implementations, the electrodes 115a and 115b may be formed from gold.

Figure 2:
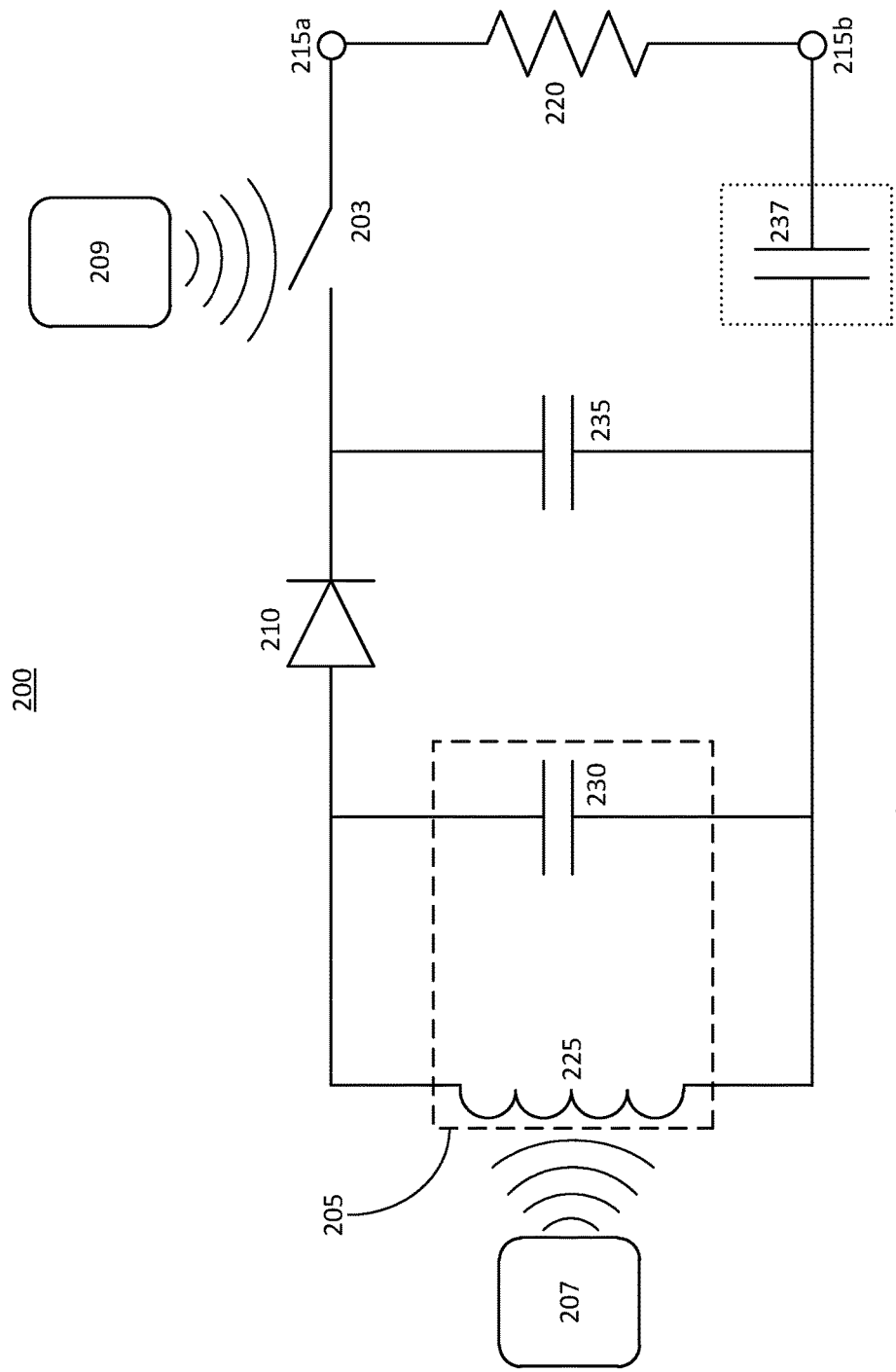
FIG. 2 shows a schematic diagram of another example neural implant device, according to an illustrative implementation.

FIG. 2 shows a schematic diagram of another example neural implant device 200, according to an illustrative implementation. The device 200 includes many of the features discussed above in connection with the device 100 shown in FIG. 1, and like reference numerals refer to like elements. For example, the device 200 includes an energy harvesting circuit 205, which in this implementation is formed from an inductor 225 in parallel with a capacitor 230. The energy harvesting circuit 205 receives a signal from a power signal generator 207, and generates an electrical signal that is rectified by the diode rectifier 210, which is positioned in series with the energy harvesting circuit 205. In addition, the device 200 includes a charge storage capacitor 235, a switch 203, and an actuation signal generator 209. The device 200 may also include a capacitor 237. The broken line surrounding the capacitor 237 indicates that the capacitor 237 is an optional component.

The charge storage capacitor 235 is configured to store electrical charge that exists across the charge storage capacitor 235 in response to the rectified signal produced by the diode rectifier 210. When the switch 203 is open, charge stored by the charge storage capacitor 235 has no path through which to be discharged. As a result, charge will accumulate across the charge storage capacitor 235 while a rectified signal is present at the output of the diode rectifier 210, and the charge storage capacitor 235 will retain the accumulated charge until the switch 203 is closed. It should be noted that, while a charge storage capacitor 235 is shown in FIG. 2, in some implementations, another charge storage element could be substituted. For example, a rechargeable battery could be used as a charge storage element in the device 200 instead of the charge storage capacitor 235.

When the switch 203 is closed, the charge stored by the charge storage capacitor 235 can be discharged through the nervous tissue 220 via the exposed electrodes 215a and 215b. Thus, a neural stimulation pulse is only provided to the nervous tissue 220 when the switch 203 is closed. By selectively opening and closing the switch 203, a selected pattern of neural stimulation pulses can be delivered to the nervous tissue 220. In some implementations, the actuation signal generator 209 can be configured to selectively open and close the switch 203 to generate such a pattern of neural stimulation pulses. For example, the switch 203 can be a normally open switch that is configured to close only in response to an applied actuation signal, which may be a wireless signal. The actuation signal generator 209 can transmit an actuation signal that causes the switch 203 to close temporarily, thereby allowing the voltage stored by the charge storage capacitor 203 to be discharged through the nervous tissue 220. One example implementation of the switch 203 is discussed further below in connection with FIG. 3.

In some implementations, the addition of the charge storage capacitor 235 and the switch 203 may counterintuitively allow the size of the device 200 to be reduced relative to the size of the device 100 shown in FIG. 1, which does not include these components. For example, attempting to reduce the sizes of the wires and components of the device 100 shown in FIG. 1 results in increased electrical resistance, and decreased instantaneous power of the neural stimulation pulse received by the nervous tissue 120. Incorporating the charge storage capacitor 235 allows for the accumulation of a larger amount of electrical energy in the device 200, which can be discharged through the tissue 220 in a short pulse by momentarily closing the switch 203. Thus, the device 200 can be capable of transmitting short pulses at a higher average power than the average power of the neural stimulation signal produced by the device 100 shown in FIG. 1. As a result, the components of the device 200 can be made smaller and the device 200 can still be capable of delivering neural stimulation pulses of sufficient power, even when taking into account the increased electrical resistance that may occur due to the relatively smaller components.

In some implementations, the switch 203 can be configured to close for a duration of time equal to a desired duration of the neural stimulation pulse. For example, in some implementations, the desired duration of the neural stimulation pulse may be about 0.1 milliseconds, about 0.2 milliseconds, about 0.3 milliseconds, or about 0.4 milliseconds. The neural stimulation pulse may have a charge output (i.e., an integrated current) in the range of about 5 nC to about 15 nC and a voltage in the range of about 0.5 volts to about 1.5 volts. In some implementations, the neural stimulation pulse may have a charge output of about 10 nC and a voltage of about 1 volt.

The device 200 also can be individually activated independently of other such devices 200 that may also be implanted within the patient. For example, the switch 203 can be configured to respond to an actuation signal that differs from an actuation signal associated with the switch of another implantable device. Thus, multiple instances of the device 200 can be implanted in the patient, and each can be activated independently to achieve a desired therapeutic effect. In some implementations, a group of two or more devices 200 may be configured to respond to the same actuation signal, such that the group of devices 200 can be activated simultaneously. Other devices 200 not in the group may be configured to respond to a different actuation signal, so that activation of the devices within the group can be achieved independently of activation of the devices not within the group. An example of a system including multiple instances of the device 200 is described further below in connection with FIG. 4.

In some implementations, the optional capacitor 237 may be added to the system 200 to cause the integrated average current through the stimulation electrodes 215a and 215b to be zero. Zero average DC current can help to preserve the impedance properties of some types of neural electrodes, and also may reduce corrosion, pH changes, and local tissue damage as well.

In some implementations, various components of the device 200 may be included on a single chip, which can help to reduce the overall size of the device 200. For example, in some implementations, the diode rectifier 210 and one or both of the capacitors 235 and 237 may be included on a single chip. In general, any two or more of the diode rectifier 210, the inductor 225, the capacitor 230, the capacitor 235, and the capacitor 237 may be included on a single chip.

Figure 3:
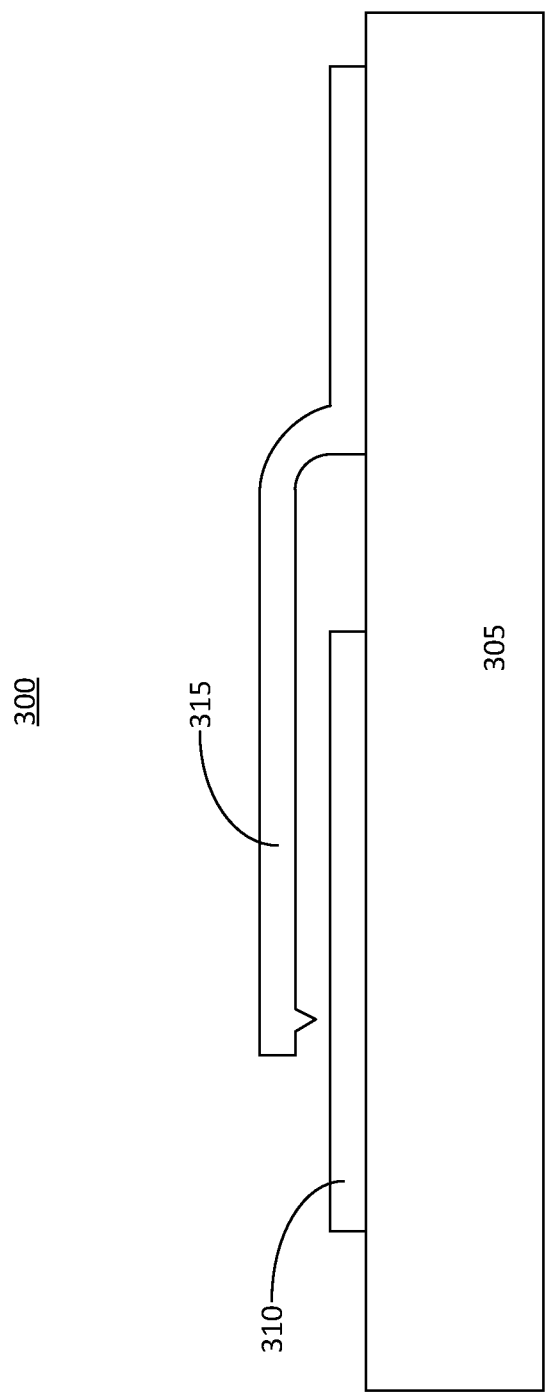
FIG. 3 shows a cross-sectional view of a MEMS reed switch that can be used in the neural implant device of FIG. 2, according to an illustrative implementation.

FIG. 3 shows a cross-sectional view of a microelectromechanical systems (MEMS) reed switch 300 that can be used in the neural implant device of FIG. 2, according to an illustrative implementation. For example, the MEMS reed switch 300 can serve as the switch 203 shown in FIG. 2. The MEMS reed switch 300 is a single-pole, single-throw switch including a substrate 305, a first contact 310, and a second contact 315. The substrate 305 is formed from a non-magnetic material, while the first contact 310 and the second contact 315 are formed from a magnetic material, such as an iron-nickel alloy. Alternatively, the switch may be electrostatically actuated by the voltage stored on capacitor 235, discharging a pulse whenever the voltage across the switch 203 reaches a level sufficient to actuate the switch.

As shown, the second contact 315 is fixed to the substrate 305 at one end, and the other end of the second contact 315 is suspended above the first contact 310 such that the MEMS reed switch 300 is normally open. When a magnetic field of sufficient amplitude along the long direction of the switch is applied in the vicinity of the MEMS reed switch 300 at a frequency that matches a resonant frequency of the second contact 315, the second contact 315 bends downwards to touch the first contact 310, thereby closing the switch 300. In some implementations, when the MEMS reed switch 300 serves as the switch 203 shown in FIG. 2, the first contact 310 can be electrically connected to the output of the diode rectifier 210 and the second contact can be electrically connected to the electrode 215a, as shown in the schematic of FIG. 2. In some implementations, the MEMS reed switch 300 may be configured to close in response to a magnetic field having a frequency that differs from a frequency associated with a different MEMS reed switch 300. This configuration can allow multiple instances of the MEMS reed switch 300 to be actuated independently. In some implementations, the MEMS reed switch 300 can exhibit hysteresis, such that it closes at a higher amplitude magnetic field than is required for it to remain closed. In such implementations, the MEMS reed switch 300 may be operated with a combined DC plus AC magnetic field. The DC field can be selected to be strong enough to hold the MEMS reed switch 300 in a closed position, and the AC field can be tuned to the resonant frequency of selected stimulation nodes.

The MEMS reed switch 300 also can be selected to have a resonant frequency different from the resonant frequency of the generated by the power signal generator 207 shown in FIG. 2, so that the MEMS reed switch 300 will not accidentally close in response to the signal generated by the power signal generator 207. As discussed above, the signal generated by the power signal generator 207 may be in the range of about 100 kHz to about 100 MHz. In some implementations, the resonant frequency of the MEMS reed switch 300 may be significantly lower than the frequency of the signal generated by the power signal generator 207. For example, the resonant frequency of the MEMS reed switch 300 may be in the range of about 1 kHz to about 50 kHz. In some implementations, the resonant frequency of the MEMS reed switch 300 may be about 10 kHz. The frequency of the signal generated by the actuation signal generator 209 shown in FIG. 2 can be selected to match the resonant frequency of the MEMS reed switch 300. Thus, in some implementations, the frequency of the signal generated by the actuation signal generator 209 may be in the range of about 1 kHz to about 50 kHz.

It should be noted that the MEMS reed switch 300 is illustrative only, and in some implementations, the switch 203 may be implemented as a different type of switch. For example, the switch 203 may instead be implemented as an electrostatic relay configured to close at a threshold voltage. Thus, when the voltage across the charge storage capacitor 235 shown in FIG. 2 exceeds the threshold voltage associated with the electrostatic relay, the electrostatic relay will close, which allows the charge storage capacitor 235 to be discharged to produce a neural stimulation pulse. After the charge storage capacitor 235 is discharged, the voltage across the charge storage capacitor will again fall below the threshold voltage, and the electrostatic relay will open.

Figure 4:
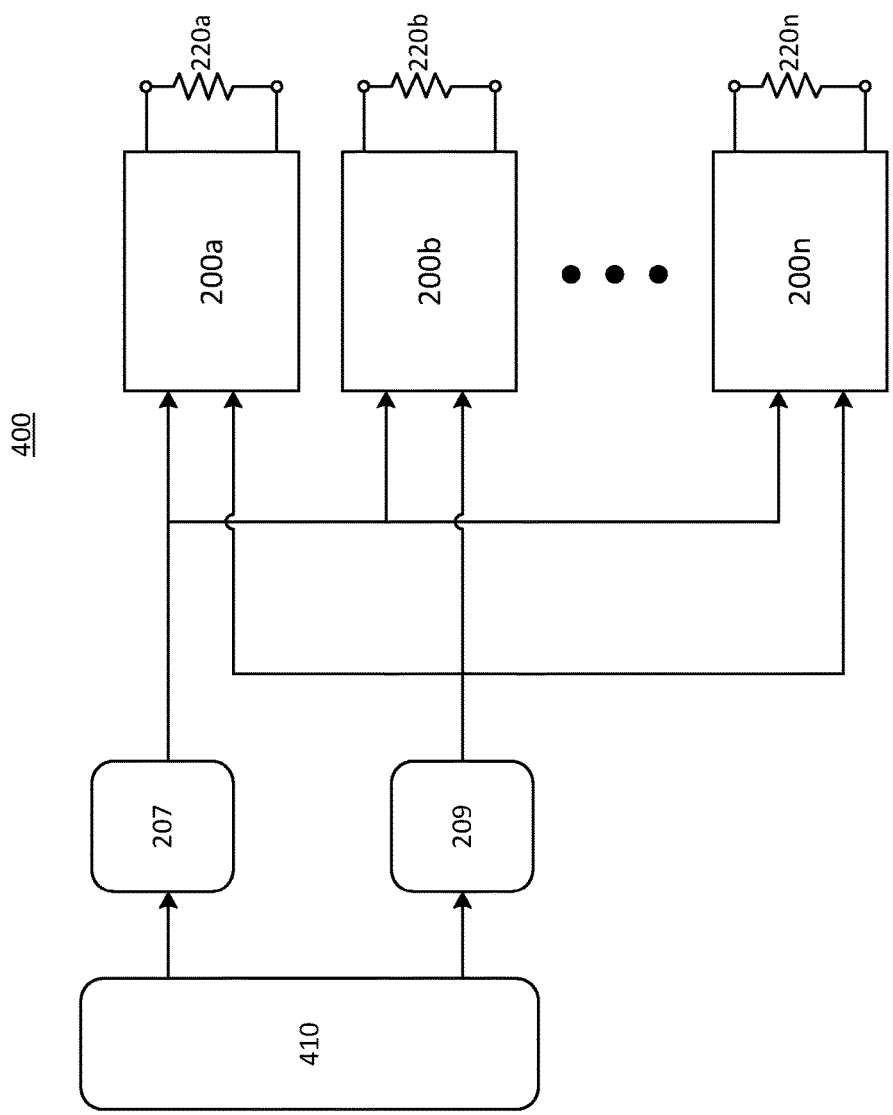
FIG. 4 shows a system including multiple instances of the neural implant device shown in FIG. 2, according to an illustrative implementation.

FIG. 4 shows a system 400 including multiple instances of the neural implant device shown in FIG. 2, according to an illustrative implementation. As shown, the system 400 includes implantable devices 200a-200n (generally referred to as devices 200), each of which is associated with a respective portion of nervous tissue 220a-220n (generally referred to as nervous tissue 220). A power signal generator 207 and an actuation signal generator 209 communicate with each of the devices 200. A controller 410 communicates with each of the power signal generator 207 and the actuation signal generator 209.

The system 400 can include any number of devices 200. In some implementations, the system 400 may include tens, hundreds, or thousands of the devices 200, all of which may be implanted into a patient. In some implementations, all of the devices 200 may be implanted near a single target muscle, nerve, brain structure, or other nervous tissue. In some other implementations, a subset of the devices 200 may be implanted near a first targeted portion of muscle, nervous tissue, and another subset of the devices 200 may be implanted near a second targeted portion of nervous tissue. In some implementations, some or all of the devices 200 may be implanted substantially simultaneously. For example, a plurality of devices 200 may be loaded into a syringe, and injected into the patient near the targeted muscle or nervous tissue. In some other implementations, the devices 200 may each be implanted within the patient separately.

The devices 200 may be used to treat any condition that can benefit from neural stimulation. For example, the devices 200 may be implanted in the brain for cortical or deep-brain stimulation. In some other implementations, the devices 200 may be implanted into peripheral nerves. Stimulation of peripheral nerves can help to treat conditions such as chronic pain, high-blood pressure, or hormonal imbalance. Additionally, using a plurality of devices 200 as shown in FIG. 4, rather than a single device 200, can help to improve the efficacy of neural stimulation treatment. The devices 200 may be used to stimulate muscles to compensate for damaged or severed nerves, as part of a system to restore motion to a patient.

The devices 200 can be individually activated to achieve a desired therapeutic effect. For example, it may be desirable to activate only the subset of devices 200 that are positioned near a first targeted portion of nervous tissue without activating other devices 200 that may be implanted elsewhere. As discussed above in connection with FIG. 2, each device 200 can be activated by closing the switch 203 that allows the charge storage capacitor 235 to be discharged. By appropriately selecting switches 203 that respond to different actuation signals, the system 400 can be configured such that a desired subset of the devices 200 can be activated simultaneously without activating the devices 200 that are not part of the desired subset. Therefore, all of the devices 200 that are implanted near the first targeted portion of nervous tissue may include switches 203 that respond to an actuation signal having a particular frequency. The controller 410 can cause all of the devices 200 near the first targeted portion of nervous tissue to generate neural stimulation pulses substantially simultaneously by controlling the actuation signal generator 209 to generate an actuation signal with a frequency that matches the frequency associated with switches 203 of the devices 200 that are positioned near the first targeted portion of nervous tissue. Other devices 200 that are not intended to stimulate the first targeted portion of nervous tissue may include switches that actuate in response to an actuation signal having a different frequency.

The above configuration can make use of a simple power signal generator 207, because the triggering of the neural stimulation pulses is managed independently of the energy harvesting. As a result, the power signal generator can emit a constant input signal configured to be converted into an electrical signal by all of the devices 200, even during periods in which it is desired that some of the devices 200 do not deliver a neural stimulation pulse. All of the devices 200 can therefore simultaneously harvest energy from the signal provided by the power signal generator 207. The controller 410 can cause the energy stored by the devices 200 to be selectively discharged to produce neural stimulation pulses by commanding the actuation signal generator 209 to produce actuation signals according to a desired neural stimulation scheme.

Figure 5:
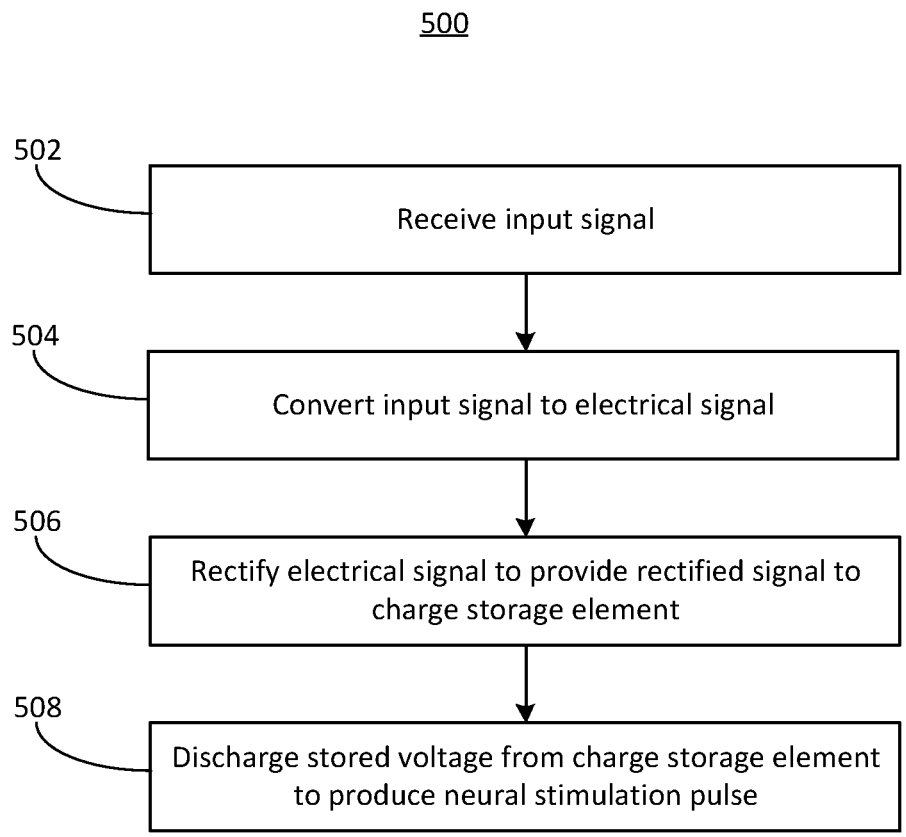
FIG. 5 shows a block diagram of an example method for delivering a neural stimulation pulse, according to an illustrative implementation.

FIG. 5 shows a block diagram of an example method 500 for delivering a neural stimulation pulse, according to an illustrative implementation. In brief overview the method 500 includes receiving a an input signal (stage 502). The input signal is converted to an electrical signal (stage 504). The electrical signal is rectified to provide a rectified signal to a charge storage element (stage 506). A voltage is discharged from the charge storage element to produce a neural stimulation pulse (stage 508).

In some implementations, the method 500 can be carried out by the implantable neural stimulation device 200 shown in FIG. 2. For example, with reference to FIGS. 2 and 5, the energy harvesting circuit 205 can receive an input signal from a power signal generator 207 (stage 502). The input signal can be, for example, a magnetic signal whose frequency matches the resonant frequency of the inductor 225 and the capacitor 230 that form the energy harvesting circuit 205. As a result of the resonance, the energy harvesting circuit 205 can convert the input signal received from the power signal generator 207 into an electrical signal (stage 504). The diode rectifier 210 can receive the electrical signal from the energy harvesting circuit 205, and can rectify the signal to provide a rectified signal to the charge storage capacitor 235 (stage 506). The rectified signal causes charge to accumulate across the charge storage capacitor 235. By selectively closing the switch 203, the voltage stored by the charge storage capacitor can be discharged to produce a neural stimulation pulse that is delivered to the nervous tissue 220 via the electrodes 215a and 215b (stage 508).

Various modifications to the implementations described in this disclosure may be readily apparent to those skilled in the art, and the generic principles defined herein may be applied to other implementations without departing from the spirit or scope of this disclosure. Thus, the claims are not intended to be limited to the implementations shown herein, but are to be accorded the widest scope consistent with this disclosure, the principles and the novel features disclosed herein.

Certain features that are described in this specification in the context of separate implementations also can be implemented in combination in a single implementation. Conversely, various features that are described in the context of a single implementation also can be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Further, the drawings may schematically depict one more example processes in the form of a flow diagram. However, other operations that are not depicted can be incorporated in the example processes that are schematically illustrated. For example, one or more additional operations can be performed before, after, simultaneously, or between any of the illustrated operations. In certain circumstances, multitasking and parallel processing may be advantageous. Moreover, the separation of various system components in the implementations described above should not be understood as requiring such separation in all implementations. Additionally, other implementations are within the scope of the following claims. In some cases, the actions recited in the claims can be performed in a different order and still achieve desirable results.

What is claimed is:

1. A neural implant device, comprising:
   an energy harvesting circuit configured to receive an input signal and generate an electrical signal based on the received input signal;
   a diode rectifier in series with the energy harvesting circuit, the diode rectifier configured to rectify the electrical signal, wherein the energy harvesting circuit and the diode rectifier are encapsulated within a biocompatible electrically insulating material;
   a neural electrode exposed through the biocompatible electrically insulating material, the neural electrode configured to deliver a neural stimulation pulse;
   an energy storage device configured to store a charge from an output of the diode rectifier; and
   a switch configured to discharge the stored charge to the neural electrode when the switch is in a closed position, the switch configured to close in response to a wireless actuation signal having an AC component, the wireless actuation signal being of a different frequency than a resonant frequency of the energy harvesting circuit;
   the neural implant device having a volume that is less than about 1 cubic millimeter.

2. The neural implant of claim 1, wherein the energy harvesting circuit comprises an inductor in parallel with a capacitor.

3. The neural implant of claim 2, wherein the inductor has an inductance in a range of about 10 nH to about 500 µH.

4. The neural implant of claim 2, wherein the inductor comprises a coil made from at least one of copper, aluminum, silver or gold wound around a ferrite core, wherein the coil is wound within the biocompatible electrically insulating material, and the biocompatible electrically insulating material is substantially free from air bubbles.

5. The neural implant of claim 2, wherein the inductor has a diameter that is no greater than about 0.4 millimeters and a length that is no greater than about 1.0 millimeters.

6. The neural implant of claim 2, wherein the capacitor has a capacitance in a range of about 1 pF to about 10 nF.

7. The neural implant of claim 2, wherein the capacitor and the inductor form a circuit having a resonant frequency in a range of about 100 kHz to about 100 MHz.

8. The neural implant of claim 2, wherein at least two of the capacitor, the inductor, and the diode rectifier are included on a single chip.

9. The neural implant of claim 1, wherein the first switch is a normally open switch configured to close in response to the wireless actuation signal.

10. The neural implant of claim 9, wherein the switch exhibits hysteresis, such that an amplitude of the wireless actuation signal required to close the switch is greater than an amplitude of the wireless actuation signal required to hold the switch in a closed position.

11. The neural implant of claim 10, wherein the wireless actuation signal further comprises a DC component selected to be of sufficient to magnitude to hold the switch in a closed position, and
   the AC component has a frequency that matches a resonant frequency of the switch, wherein a sum of amplitudes of the DC component and the AC component is sufficient to close the switch.

12. The neural implant device of claim 1, wherein the neural implant device has a volume that is less than about 0.5 cubic millimeters.

13. The neural implant of claim 1, wherein the biocompatible electrically insulating material comprises at least one of parylene, silicone, and epoxy.

14. The neural implant of claim 1, wherein the energy harvesting circuit comprises at least one piezoelectric energy harvester.

15. The neural implant of claim 1, wherein the first switch comprises at least one of a microelectromechanical systems (MEMS) magnetic reed switch or an electrostatically actuated MEMS switch.

16. The neural implant of claim 1, further comprising an antenna coupled to the energy harvesting circuit, wherein the antenna is configured to:
    receive the input signal from a transmitter; and
    provide the input signal to the energy harvesting circuit.

17. A neural implant device, comprising:
    an energy harvesting circuit configured to receive an input signal and generate an electrical signal based on the received input signal;
    a diode rectifier in series with the energy harvesting circuit, the diode rectifier configured to rectify the electrical signal, wherein the energy harvesting circuit and the diode rectifier are encapsulated within a biocompatible electrically insulating material;
    a neural electrode exposed through the biocompatible electrically insulating material, the neural electrode configured to deliver a neural stimulation pulse;
    an energy storage device configured to store a charge from an output of the diode rectifier; and
    a switch configured to discharge the stored charge to the neural electrode when the switch is in a closed position, the switch being a normally open switch configured to close in response to a wireless actuation signal, the switch exhibiting hysteresis such that an amplitude of the wireless actuation signal required to close the switch is greater than an amplitude of the wireless actuation signal required to hold the switch in a closed position.

18. The neural implant of claim 17, wherein the energy harvesting circuit comprises an inductor in parallel with a capacitor.

19. The neural implant of claim 18, wherein the inductor has a diameter that is no greater than about 0.4 millimeters and a length that is no greater than about 1.0 millimeters.

20. The neural implant of claim 18, wherein at least two of the capacitor, the inductor, and the diode rectifier are included on a single chip.

21. The neural implant device of claim 17, wherein the neural implant device has a volume that is less than about 1 cubic millimeter.

22. The neural implant device of claim 21, wherein the neural implant device has a volume that is less than about 0.5 cubic millimeters.

23. The neural implant of claim 17, wherein the energy harvesting circuit has a resonant frequency in a range of about 100 kHz to about 100 MHz.

24. The neural implant of claim 23, wherein the switch is configured to close in response to a wireless actuation signal having a frequency in a range of about 1 kHz to about 50 kHz.

25. The neural implant device of claim 17, wherein the diode rectifier has a turn-on voltage of less than about 0.3 volts.

26. The neural implant of claim 17, wherein the energy harvesting circuit comprises at least one piezoelectric energy harvester.

27. The neural implant of claim 17, wherein the switch comprises at least one of a microelectromechanical systems (MEMS) magnetic reed switch or an electrostatically actuated MEMS switch.

28. The neural implant of claim 17, wherein the wireless actuation signal comprises:
    a DC component selected to be of sufficient to magnitude to hold the switch in a closed position; and
    an AC component having a frequency that matches a resonant frequency of the switch, wherein a sum of amplitudes of the DC component and the AC component is sufficient to close the switch.

29. The neural implant of claim 17, further comprising an antenna coupled to the energy harvesting circuit, wherein the antenna is configured to:
    receive the input signal from a transmitter; and
    provide the input signal to the energy harvesting circuit.

30. The neural implant device of claim 17, wherein the neural stimulation pulse has a charge output in a range of about 5 nC to about 15 nC and a voltage in a range of about 0.5 volts to about 1.5 volts.

* * * * *

UNITED STATES PATENT AND TRADEMARK OFFICE
CERTIFICATE OF CORRECTION

PATENT NO. : 10,039,923 B2
APPLICATION NO. : 15/014675
DATED : August 7, 2018
INVENTOR(S) : Jonathan J. Bernstein et al.

Page 1 of 1

It is certified that error appears in the above-identified patent and that said Letters Patent is hereby corrected as shown below:

In the Claims

Column 12, Claim 9, Line number 52, delete "first".

Column 13, Claim 15, Line number 10, delete "first".

Signed and Sealed this
Eighteenth Day of September, 2018

Andrei Iancu
*Director of the United States Patent and Trademark Office*